(12) United States Patent
Wright et al.

(10) Patent No.: US 7,140,232 B2
(45) Date of Patent: Nov. 28, 2006

(54) METHOD AND APPARATUS FOR MULTIPLE GAS SENSOR

(75) Inventors: Kenneth Wright, Bridgton, ME (US); Jeffrey M. Pollard, Gray, ME (US); Gary Broniarczyk, Fryeburg, ME (US)

(73) Assignee: Radiodetection Limited, Bristol (GB)

( * ) Notice: Subject to any disclaimer, the term of this patent is extended or adjusted under 35 U.S.C. 154(b) by 0 days.

(21) Appl. No.: 10/319,814

(22) Filed: Dec. 16, 2002

(65) Prior Publication Data

US 2004/0112117 A1   Jun. 17, 2004

(51) Int. Cl.
*G01N 25/00*   (2006.01)
*G01M 3/04*   (2006.01)

(52) U.S. Cl. ..................... 73/25.01; 73/40.7
(58) Field of Classification Search ............... 73/23.35, 73/25.01, 23.32, 31, 33, 40.7
See application file for complete search history.

(56) References Cited

U.S. PATENT DOCUMENTS

| | | | |
|---|---|---|---|
| 3,871,827 A | 3/1975 | Seiler et al. ............... 23/254 R |
| 4,054,414 A * | 10/1977 | Grob et al. .................. 436/115 |
| 4,121,455 A * | 10/1978 | Haslett et al. ........... 73/861.04 |
| 4,269,059 A * | 5/1981 | Baker ...................... 73/863.03 |
| 4,304,752 A | 12/1981 | Jenkins et al. ................ 422/98 |
| 4,530,817 A * | 7/1985 | Holter et al. ............... 422/122 |
| 4,576,054 A * | 3/1986 | Lalin ........................ 73/863.03 |
| 4,590,796 A * | 5/1986 | Baatz .......................... 73/113 |
| 4,668,635 A * | 5/1987 | Forster ...................... 436/134 |
| 5,116,356 A * | 5/1992 | Ohkubo et al. ......... 123/406.43 |
| 5,265,459 A * | 11/1993 | Cohen ...................... 73/25.03 |
| 5,343,700 A * | 9/1994 | Fujimoto et al. .............. 60/276 |
| 5,400,642 A * | 3/1995 | Salvador Palacios et al. ........................... 73/23.2 |
| 5,788,832 A * | 8/1998 | Howard et al. ............. 205/775 |
| 5,842,339 A * | 12/1998 | Bush et al. ................. 73/118.1 |
| 5,916,294 A * | 6/1999 | Naber et al. ............... 73/23.31 |
| 5,941,928 A * | 8/1999 | Naber et al. ............... 73/118.1 |
| 6,112,574 A * | 9/2000 | Hirano et al. .............. 73/23.31 |
| 6,176,125 B1 * | 1/2001 | Hirano et al. .............. 73/118.1 |
| 6,196,056 B1 | 3/2001 | Ewing et al. ................. 73/40.7 |
| 6,312,328 B1 * | 11/2001 | Nakajima et al. ........... 454/187 |
| 6,367,320 B1 * | 4/2002 | Kueper et al. ............. 73/118.1 |
| 2002/0129547 A1 * | 9/2002 | Chiu .......................... 47/65.5 |

FOREIGN PATENT DOCUMENTS

| | | |
|---|---|---|
| DE | 19503783 | 8/1996 |
| EP | 1166845 | 1/2002 |
| GB | 1303708 | 1/1973 |
| JP | 11023403 | 1/1999 |

OTHER PUBLICATIONS

"Carulite Catalyst"; Carus Chemical Company; Aug. 2, 2002; XP002277626; pp.; 1-8; retrieved on Apr. 21, 2004 via internet <URL:http://www.caruschem.com/pdf/new_files/Carulite.pdf.pdf>.

* cited by examiner

*Primary Examiner*—Hezron Williams
*Assistant Examiner*—John Fitzgerald
(74) *Attorney, Agent, or Firm*—Baker & Hostetler LLP

(57) ABSTRACT

A method and apparatus includes filter for removing a non-tracer gas from detection system and control unit for detecting the presence a low concentration tracer gas in the atmosphere.

19 Claims, 3 Drawing Sheets

METHOD AND APPARATUS FOR MULTIPLE GAS SENSOR

FIELD OF THE INVENTION

The present invention relates generally to a method and apparatus for detecting a gas. More particularly, the present invention relates to improved detection of tracer gases using an improved gas chromatograph and catalyst.

BACKGROUND OF THE INVENTION

Utilities including; underground water lines, gas lines, air pressurized telephone cables, pressurized vessels or any apparatus where containment is a consideration, can develop leaks.

Unfortunately, there are times when the containment is penetrated, either by chemical degradation (electrolysis), mechanical stresses, or similar phenomena. These penetrations cause leaks in the system and permit water to seep inside or the systems contents to leak out.

Discovering and repairing this damage can cost the provider substantial sums of money. One of the reasons is that it is sometimes necessary to excavate in several points. Another reason is that it might be necessary to unearth hundreds of yards of an underground system due to the impossibility of identifying the exact location of the leak.

There have been a number of techniques used to aid the provider in more accurately pinpointing the area of breakage. One technique that has enjoyed a period of success is the technique of obtaining a preliminary rough location of the leak by taking pressure measurements along the system and calculating the leaks position based on pressure changes. However, the problem with this technique is the range of detection, which can be anywhere from 300 feet to 6,000 feet.

Another technique is to incorporate the above prior art and in addition introduce a detectable tracer gas into the containment system. The tracer gas (like helium or hydrogen) mixes with the contents of the system with a natural or induced flow. The tracer gas escapes the containment through the leak and rapidly rises upwardly and becomes detectable outside the containment or at the surface of the ground if buried. A mass spectrometer is then used to detect the tracer gas. The problem with the spectrometers is that their operation depends upon separation of the tracer gas in a vacuum by imparting an electrical charge to the gas sample containing the tracer gas. The sample is pushed through a magnetic field, and the ions collected from the results. The electronics in such a device include a supply of high voltage and the vacuum system. All of these components tend to make the mass spectrometer bulky, complicated and expensive. With this type of equipment, it is difficult to operate in areas where access to such heavy equipment can be difficult.

An additional problem with the prior art was the ability to accurately detect the tracer gas. In many of the prior art devices, other non-tracer gases had the ability to set-off the detector in a manner undistinguishable from the tracer gas, hence, causing false readings.

An additional problem with the prior art is the affect that humidity has upon the accuracy of the detection of the tracer gas. Increased humidity decreases the ability of the sensor to detect the tracer gas in low concentrations.

Accordingly, it is desirable to provide a lightweight detector that can more accurately detect a tracer gas, and not produce false readings in the presence of non-tracer gas or elevated humidity.

SUMMARY OF THE INVENTION

One aspect of the present invention is to provide a combination of filters that are attached to the detector in order for it to accurately detect the presence of a tracer gas.

In another aspect of the present invention, a higher sensitivity is provided in the presence of a lower concentration of a tracer gas.

The above is achieved through the use of a novel combination of filters, a control unit and a tracer gas sensor as herein disclosed. In accordance with one embodiment of the present invention, a gas detector includes a catalyst filter, and absorption filter, a control unit linked to the absorption filter and a gas sensor linked to the control unit. A further element can include a humidity filter attached to the catalyst filter.

The gas sensor is sensitive to the change in gas thermal conductivity as compared to air. In this embodiment, a thermistor is employed.

The control unit includes a pump linked to the humidity filter, linked to the catalyst filter, linked to an absorption filter attached to the first side of the gas sensor and a screen filter attached to a second side of the gas sensor. The screen filter is used to prevent insects or other debris from entering the system. The control unit can also include an air outlet linked to the screen filter.

In this embodiment, the humidity filter is multi-stage. The stages are layers of activated alumnia, silica gel, and activated alumnia. The humidity filter is used to maintain and extend the useful life of the catalyst filter as well as reduce the effects of humidity on the sensing process.

In an alternate embodiment of the present invention, a method for detecting a tracer gas provides the steps of passing an air sample through a catalyst filter and an absorption filter, determining the presence of a tracer gas in the air and alerting a user as to the detection of the tracer gas in the air sample. A further step can include passing the air sample through a humidity filter. In this alternate embodiment, the humidity filter is placed prior to the catalyst filter.

In order to determine the tracer gas, the air is pumped through the control unit and passed over the sensor. Once this is done, a differential voltage reading is taken and compared to a fixed reference point. The fixed reference point, in this alternate embodiment, is a second thermistor, which monitors the ambient air not exposed to the tracer gas airstream.

In another alternate embodiment, an apparatus for detecting a tracer gas includes means for passing air through an absorption filter, means for determining the presence of helium gas in the air and means for alerting a user as to the detection of the tracer gas in the air sample. A further element can include means for passing the air through a humidity filter and catalyst filter. In this embodiment, the air is passed through a humidity filter prior to the catalyst filter and then through the absorption filter.

To detect the presence of helium or hydrogen, the means for determining the presence of helium or hydrogen gas includes means for passing the air sample over means for sensing. Once this is accomplished, means for comparing the voltage differential due to the temperature change of the means for sensing to a reference point is conducted. The means for sensing can be a thermistor. The reference point can be a second thermistor, which references the ambient air temperature.

In another alternate embodiment, an apparatus for detecting a tracer gas includes a control unit, a catalyst filter attached externally to the control unit and a humidity filter attached to the catalyst filter. The control unit provides a gas sensor and a pump. Attached to the pump is a catalyst filter to ensure that the environmental gas emissions do not accidentally trip the detector.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

A preferred embodiment of the present invention provides a filtering system and a low concentration sensitivity to detect a tracer gas that is pumped through a system.

Figure 1:
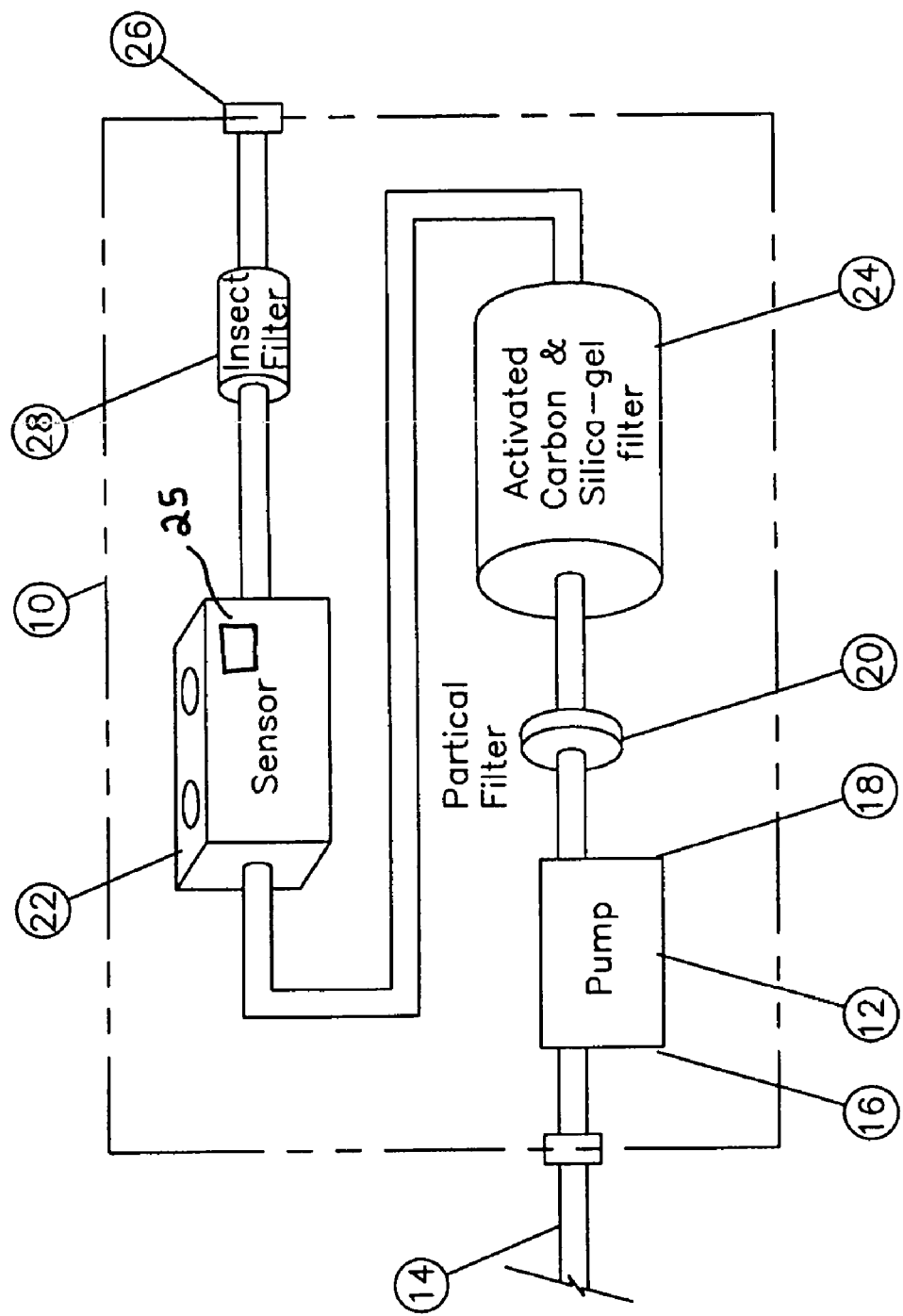
FIG. 1 provides an illustration of several elements of a preferred embodiment of the present invention.

A preferred embodiment of the present inventive apparatus and method is illustrated in FIG. 1. FIG. 1 illustrates a control unit portion 10 of the present invention. A pump 12 draws an air sample from outside of the device and into the control unit 10. The sample air is drawn through a tube 14 that extends from a first side 16 of the pump 12. As the sample air is drawn into the pump 12, the second side 18 of the pump 12 pushes the sample air toward the remaining components of the control unit 10.

As the sample air is pushed out of pump 18, it enters a particle filter 20. The purpose of the particle filter 20 is to smooth or even out the pulsing of the pump 12 for the sensor 22. This enables the sensor 22 to receive a sample of air on a continuous basis rather than a pulsed air stream.

After the particle filter 20, the air is sent through carbon filter 24. The carbon filter's 24 purpose is to remove carbon dioxide from the air sample. By removing the carbon dioxide from the air sample, the sensor 22 is less likely to report false detections. The carbon filter is comprised of activated carbon particles and silica gel. The silica gel is to prevent caking of the carbon particles from excessive water vapor.

From the carbon filter 24, the air is pumped into the sensor 22. In the preferred embodiment, the sensor 22 is two balanced thermistors, which are built into an aluminum block. A thermistor is a thermally sensitive resistor of which its primary function is to exhibit a change in resistance accompanying with a change in temperature.

One of the thermistors is exposed to the air sample being drawn and pumped through the sensor 22. The other thermistor is a reference thermistor that is only exposed to the ambient air that is inside the control unit 10. The reference thermistor is not exposed to the air sample being pumped through the control unit 10.

A comparative circuit monitors the voltage differential of both thermistors. As the tracer gas, such as helium or hydrogen, is passed over the gas sensor 22, it cools the temperature of the thermistor. The reference thermistor is using the temperature of the ambient air as a reference point to which the air sample is compared. A gas that has a higher or lower thermal conductivity based upon reference table is detected by the gas sensor 22. In other words, as the air sample is passed over the sensor 22, the temperature of the thermistor is monitored on a continuous basis. The measured voltage differential is compared with a comparator circuit and the result referenced against a known set of data. If the result falls within certain known voltage changes that occur in the presence of the tracer gas, then the comparator alerts the user as to the detection of the tracer gas.

In the preferred embodiment, the control unit 10 is configured to detect helium and hydrogen. The control unit 10 at some point is injected with helium. The system, more especially the processing unit of the control unit 10, is configured such that it knows the atmospheric temperature that occurs when a helium air sample is passed over the thermistor. Helium has a high thermal conductivity as compared with the ambient air. The thermistor, in which the air sample is passed over, cools quickly. This is the reason that helium makes a good tracer gas. Secondly, it is an inert gas and its molecule size and weight make it ideal. As a result, it quickly rises especially through the subsurface where the system is buried. Hydrogen is also an inert gas and has a small molecule size. However, it is only safe to use in small quantities because of its explosive property. Due to this factor, hydrogen is used in small quantities by combining it with helium or nitrogen.

To discharge to the air sample, an outlet port 26 is linked to the control unit 10. To prevent particle or other debris such as bugs from entering the control unit 10 when not in use, a filter 28 is provided. This will keep debris from interfering with the operation of the device.

Figure 2:
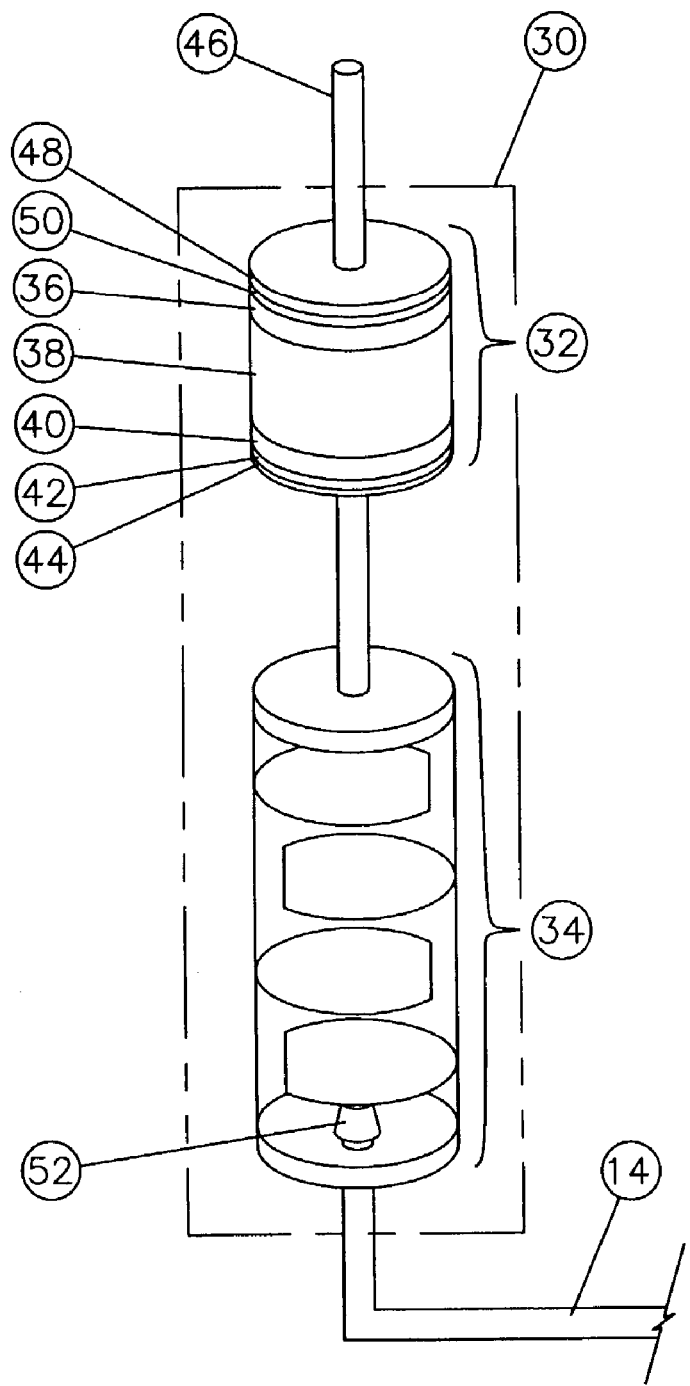
FIG. 2 provides an illustration of the filter portion of the preferred embodiment of the present invention.

FIG. 2 provides an illustration of the filter portion 30 of the preferred embodiment of the present invention. The filter portion 30 is external to the control unit 10 and not incorporated into the device itself. The filter portion 30 connects or attaches to the control unit 10 through a tube 14 that extends from the pump 12. Such a design more easily allows a technician to use it in the field. By having the filter portion 30 external to the device, the technician has more flexibility in placing the detector in hard to reach places.

The filter portion 30 is comprised a first 32 and second filter 34. The first filter 32 is a filter that removes water vapor from the air that is being drawn into the detector. In the preferred embodiment, the first filter 32 is a humidity filter, which is a multi-layer filter. The multi-layer filter is comprised of an initial layer 36 of activated alumnia, followed by a middle layer 38 of silica gel and outer layer 40 of activated alumnia. The multi-layer filter removes the moisture from the sample air in order for the second filter to operate properly.

The initial layer 36 and outer layer 40 are both activated alumnia, which is a molecular sieve or desiccant bead. A molecular sieve is a crystalline, porous, molecular structure that selectively adsorbs or rejects molecules based on differences in molecular size or shape. In the preferred embodiment, zeolites, which are one class of molecular sieves, are employed. When the air is passed through these layers 36, 40, the activated alumnia provides a means whereby the moisture is removed from the air.

The initial layer 36 is usually not enough the remove all the moisture from the air. Therefore, the preferred embodiment employs the use of another desiccant, which in this instance is a silica gel, as the middle layer 38. As the air is passed through the silica gel, additional moisture that was not removed by the initial layer 36 is removed with this layer. The silica gel provides a visual response of color change from deep blue (dry) to pink or white (wet) indicating the amount of moisture collected and the need for replacement.

Following the outer layer 40 of activated alumnia, a pad 42 and a screen 46 are used. The pad 42 and screen 44 are used to catch or stop any particulates from entering the control unit 10. If the particulates are not prevented from entering the control unit 10, these contaminants could cause a false or no detection of the tracer gas, which was used to locate a breakage in the conduit.

The air, used to detect whether there is a presence of the tracer gas, is drawn from the outside through in inlet port 46. Prior to the air being drawn into the multi-layer of the first filter 32, the air is passed through a screen 48 and a pad 50 to catch and particulates. The screen 48 and pad 50 serve as a basis for eliminating any large particle that is inadvertently drawn into the system. The particles can be leaves, bugs or any type of residue that could disrupt the operation of the detector.

The majority of buried cable lines are along thoroughfares or streets. As a result, there are a number of gases emitted from vehicles or other environmental sources that is pumped through the detector. Some of these gases can trick to the system into detecting the presence or absence of a tracer gas in the immediate area. As a result, the detector is not very reliable and can take enormous amounts of time and resources to accurately locate.

The second filter 34, in the preferred embodiment, is a baffled catalyst filter. The baffles serve to increase the contact time of the sample with the catalyst. By adding the catalyst filter, this allows the control unit 10 to be more sensitive. In other words, the control unit 10 is able to detect lower concentration amounts of the tracer gas. If the second filter 34 were not used, then the system, in order to reduce the number of false readings, would have to be adjusted to detect higher concentration amounts in the tracer gas.

The benefits of a system, where lower concentration amounts are detected, is greater accuracy for detecting the tracer gases. For example, a small breakage in a conduit emits lower amounts of the tracer gas than a larger break. In this instance, the detector 10 is able to detect the presence of the tracer gas more easily than the prior art systems.

The second filter 34, in the preferred embodiment, is a Carulite® filter. The function of the filter is to act as a catalyst and change carbon monoxide, CO, to carbon dioxide, $CO_2$. As a result, the carbon dioxide gets absorbed into the carbon filter 24, which in the preferred embodiment, is in the control unit 10.

If helium is used as the tracer gas and carbon monoxide is drawn into the system without the benefit of the Carulite® filter, the carbon monoxide passes through the carbon filter 24. The detector then becomes less sensitive to the presence of helium.

The second filter 34 also eliminates other gases, such as ozone ($O_3$), that would falsely activate the detector into reporting the presence of the tracer gas. As a result, the user begins to excavate for the breakage only to determine that the detector gave a false reading. The second filter 34, in the preferred embodiment, is the Carulite® 300 manufactured by Carus Chemical Company, 315 Fifth Street, Peru, Ill. 61354.

The first filter 32 and a second filter 34 are placed within the filter portion 30. The control unit 10 is connected to the filter portion 30 via tubing 14 in order to pump or push the sampled air through the detector. Both the first 32 and second 34 filters are removable or changeable from the filter portion 30. This enables the user to change or replace the filters as the need arises. Filter 52 is a particulate filter to prevent the migration of the filter media into the control unit 10.

Figure 3:
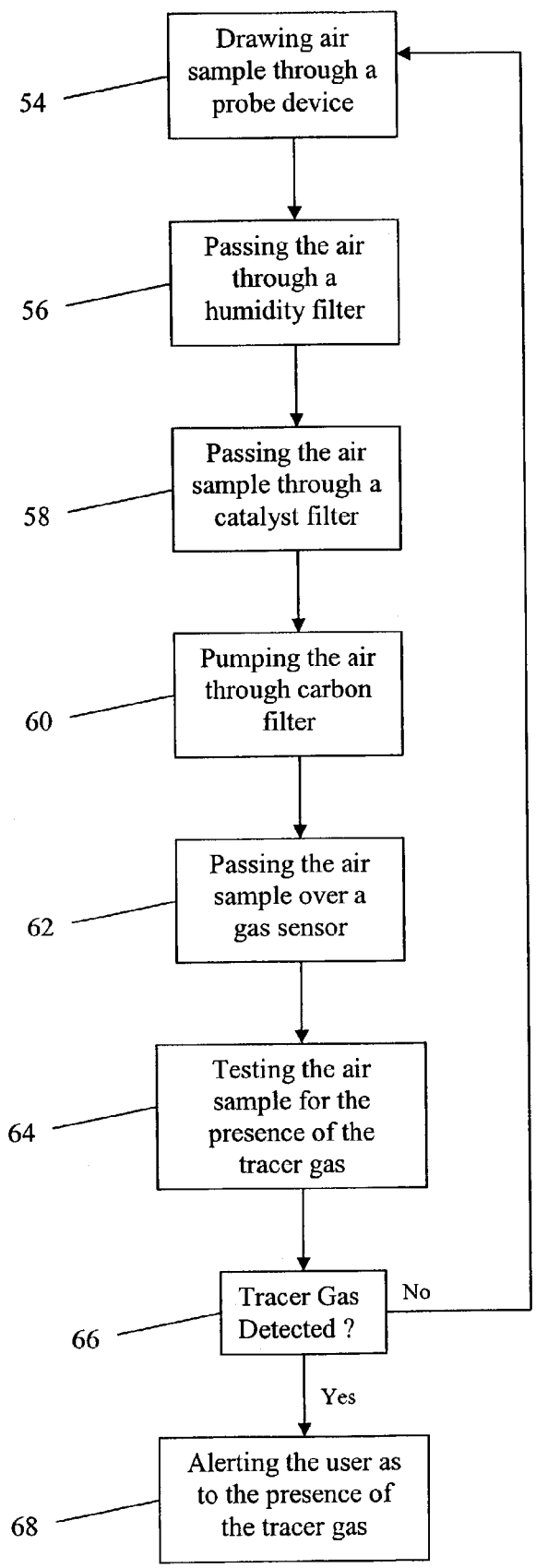
FIG. 3 is a flowchart illustrating the steps that may be followed in accordance with one embodiment of the present inventive method or process.

FIG. 3 is a flowchart illustrating the steps that may be followed in accordance with one embodiment of the present inventive method or process. The initial step in this process is the step 54 of drawing air sample through a probe device. When the air sample is drawn into the system, the next step 56 of passing it through a humidity filter is conducted. This multi-layer filter removes all moisture from the air sample. The water vapor is removed in order to accomplish the step 58 of then passing the air sample through a Carulite® filter. The purpose of this filter is to eliminate gases, such as ozone, that trip the system into falsely alerting the user of to the presence of the tracer gas.

After the air is drawn into the Carulite® filter, the next step 60 of pumping the air through a carbon filter 24 is completed. This step 60 removes other gas, such as carbon dioxide, from the control unit 10 and prevents the sensor 22 from falsely reporting the absence of the tracer gas.

After all the filter stages, the air sample, is pumped to the sensor by the next step 62. In doing this, the air sample completes the step 64 of detecting or testing whether a tracer gas is present or not. If the tracer gas is not detected, then the system repeats the process. If the tracer gas is detected, the control unit 10 performs the step 66 of alerting the user as to the presence of the tracer gas.

The many features and advantages of the invention are apparent from the detailed specification, and thus, it is intended by the appended claims to cover all such features and advantages of the invention, which fall within the true spirits, and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A gas tracer detector, comprising:
   a catalyst filter that reduces the presence of another gas other than a tracer gas from an air sample;
   a gas sensor subjected to the air sample; and
   a control unit, linked to the catalyst filter, configured to determine the presence of the tracer gas from the air sample, wherein the control unit further comprises a pump linked to the catalyst filter, a first filter attached to the pump and a first side of the gas sensor, a screen filter attached to a second side of the gas sensor, wherein the screen filter filters out debris and a second filter configured to smooth out a pulsing effect of the pump.

2. The gas tracer detector as in claim 1, wherein the control unit further comprises an air outlet linked to the screen filter.

3. The gas tracer as in claim 1, further comprising a humidity filter attached to the catalyst.

4. The gas tracer detector as in claim 3, wherein in the humidity filter is a multi-stage filter.

5. The gas tracer detector as in claim 4, wherein the humidity filter is comprised of layers of activated alumnia, silica gel and activated alumnia.

6. The gas tracer detector as in claim 1, wherein the gas sensor is sensitive to the change in air temperature.

7. The gas tracer detector as in claim 6, wherein the gas sensor is a thermistor.

8. A method for detecting a tracer gas comprising:
passing the air through a particle filter to smooth out a pulsing effect of a pump;
passing the air through a catalyst filter to reduce the presence of a gas other then the tracer gas;
subjecting the air to a gas sensor;
determining the presence of the tracer gas in the air with a control unit;
alerting a user as to the detection of the tracer gas in the air; and
comparing the temperature of the sensor to a reference point.

9. The method as in claim 8, wherein the sensor is a thermistor.

10. The method as in claim 9, wherein the reference point is a second thermistor.

11. The method as in claim 10, further comprising referencing the second thermistor to ambient air temperature.

12. The apparatus as in claim 10, further comprising referencing the second thermistor to ambient air temperature.

13. The method as in claim 8, further comprising passing the air through a humidity filter.

14. The method as in claim 13, wherein the air is passed through a humidity filter prior to the catalyst filter.

15. A-system for detecting a traceable gas comprising:
means for filtering that is configured to smooth out a pulsing effect of a pump on an air sample;
means for reducing the presence of a gas other than the traceable gas from the air sample;
means for sensing the traceable gas in the air sample;
means for determining the presence of the traceable gas in the air sample, the means for determining comprises means for passing the air over means for sensing and means for comparing a voltage differential of the means for sensing to a reference point; and
means for alerting a user as to the detection of the traceable gas in the air sample.

16. The system as in claim 15, wherein the means for sensing is a thermistor.

17. The apparatus as in claim 15, wherein the reference point is a second thermistor.

18. The system as in claim 15, further comprising means for eliminating humidity from the air sample.

19. The system as in claim 18, wherein the air sample is passed through a humidity filter prior to the catalyst filter.

* * * * *